United States Patent [19]

Jenkins

[11] 4,207,871
[45] Jun. 17, 1980

[54] SYSTEM FOR CONTROLLING THE FLOW OF INTRAVENOUS FLUIDS TO A PATIENT

[75] Inventor: Jon A. Jenkins, Rancho Santa Fe, Calif.

[73] Assignee: Imed Corporation, San Diego, Calif.

[21] Appl. No.: 913,294

[22] Filed: Jun. 7, 1978

[51] Int. Cl.² .................... A61M 5/00; A61M 1/03
[52] U.S. Cl. ...................... 128/214 R; 128/214 E; 128/214 C; 128/214 F; 128/260
[58] Field of Search ........... 128/214 R, 214 C, 214 E, 128/214 F, 260, 227

[56] References Cited

U.S. PATENT DOCUMENTS

| | | | |
|---|---|---|---|
| 2,961,965 | 11/1960 | Senning et a. | 128/214 R |
| 3,042,039 | 7/1962 | Dahlstrom | 128/227 |
| 3,049,918 | 8/1962 | Sparkuhl | 128/214 C X |
| 3,088,459 | 5/1963 | Rabinoff | 128/260 UX |
| 3,216,418 | 11/1965 | Scislowicz | 128/214 C |
| 3,521,635 | 7/1970 | Koehn | 128/214 C |
| 3,731,680 | 5/1973 | Wright et al. | 128/214 E |
| 3,896,733 | 7/1975 | Rosenberg | 128/214 R |
| 3,896,803 | 7/1975 | Mason | 128/214 R |
| 3,985,133 | 10/1976 | Jenkins et a. | 128/214 F |
| 3,994,294 | 11/1976 | Knute | 128/214 F |
| 4,155,362 | 3/1979 | Jess | 128/214 F |

*Primary Examiner*—Henry K. Artis
*Attorney, Agent, or Firm*—Ellsworth R. Roston

[57] ABSTRACT

A controller provides precisely regulated flow of intravenous fluid on a gravitational basis to a patient. The controller includes a storage chamber with first and second compartments and a diaphragm separating the compartments and movable in the chamber to vary the volumes of the first and second compartments. The storage chamber may be disposed in a replaceable cassette. Control means provide at first times for the introduction of fluid from the source to the first compartment and the passage of fluid from the second compartment to the patient. The control means provide at other times for the introduction of fluid from the source to the second compartment and the passage of fluid from the first compartment to the patient. The control means may also be included at least partially in the cassette. Means operate upon the control means, upon the movement of the diaphragm to a particular position in the second compartment, to obtain the introduction of fluid from the source to the first compartment and the passage of fluid from the second compartment to the patient. Such means operate on the control means, upon the movement of the diaphragm to a particular position in the first compartment, to obtain the introduction of fluid from the source to the second compartment and the passage of fluid from the first compartment to the patient. The control means also control at each instant the rate at which fluid flows from each of the compartments to the patient by comparing at such instant desired and actual rates of fluid flow and by providing adjustments in accordance with such comparison.

36 Claims, 4 Drawing Figures

SYSTEM FOR CONTROLLING THE FLOW OF INTRAVENOUS FLUIDS TO A PATIENT

This invention relates to a system for controlling on a precise basis the gravitational flow of intravenous fluid to a patient. More particularly, the invention relates to a controller which utilizes a replaceable cassette to provide for the passage of fluid on a gravitational basis at a precise rate to a patient.

As the practice of medicine becomes increasingly complex and increasingly refined, the equipment and techniques used to provide care for a patient have become increasingly sensitive in order to insure that the patient receives optimum care. For example, after an operation has been performed on the patient and the patient is in the recuperative state, intravenous fluid often has to be introduced to the patient. The rate of introduction of the fluid to the patient is dependent upon a number of different factors including the weight, age, sex and physical state of the patient. As the patient recovers from his illness, the rate of introduction of the intravenous fluid to the patient is adjusted to assure that the patient receives an optimum benefit from the fluid.

A considerable amount of effort has been devoted over a substantial period of time to provide a satisfactory system for controlling the rate at which fluid such as intravenous fluid is introduced to a patient. Considerable progress has been made in developing a satisfactory system for certain types of operations. For example, a system providing for the pumping of fluid on a precise volumetric basis to a patient has been disclosed and claimed in U.S. Pat. No. 3,985,133 issued on Oct. 12, 1976. This patent is assigned of record to the assignee of record of this application.

A number of fundamental problems still remain in systems providing for the flow of fluid on a gravitational basis to a patient even though a considerable effort has been devoted to the solution of such problems. For example, a satisfactory system still does not exist for providing for the introduction of fluid at a precise and predetermined rate to a patient on a gravitational basis. Furthermore, a system still does not exist which can be used on a sterile and hygienic basis for different patients such that any contamination from the use of the system for one patient would not affect the health or safety of subsequent patients.

This invention relates to a system which overcomes the above difficulties. The system provides for the flow of intravenous fluid to a patient on a gravitational basis at a precise and predetermined rate. Furthermore, the system provides a sterile and hygienic operation for individual patients so that the health of each patient will not be affected by any bacteria or illnesses from other patients.

The controller of this invention includes a storage chamber with first and second compartments and a diaphragm separating the compartments and movable in the chamber to vary the volumes of the first and second compartments. The storage member may be disposed in a replaceable cassette.

Control means provide at first times for the introduction of fluid from the source to the first compartment and the passage of fluid from the second compartment to the patient. The control means provide at other times for the introduction of fluid from the source to the second compartment and the passage of fluid from the first compartment to the patient. The control means may also be included at least partially in the cassette.

The control means operate, upon the movement of the diaphragm to a particular position in the second compartment, to obtain the introduction of fluid from the source to the first compartment and the passage of fluid from the second compartment to the patient. The control means further operate, upon the movement of the diaphragm to a particular position in the first compartment, to obtain the introduction of fluid from the source to the second compartment and the passage of fluid from the first compartment to the patient. The provision of the first and second compartments and the control of the flow of particular amounts of fluid through the first and second compartments provide for an accuracy of the rate at which fluid flows to the patient at each instant.

The controller of this invention also includes an adjustable clamp leading from an output line to a patient. Means are included in the controller for determining the rate at which fluid flows at each instant from the output line to the patient. Such determinations are compared with indications representing a desired rate of fluid flow, and an error signal is produced representing any differences between the characteristics of the signals being compared. Such error signal is introduced to the adjustable clamp to adjust the clamp in a direction for varying the flow of fluid to minimize the error signal.

The controller of this invention is particularly advantageous because it can be used with a replaceable cassette. The cassette is disclosed and claimed in copending application Ser. No. 913,282 filed by Ray Cannon and assigned of record to the assignee of record of this application. The cassette includes the chamber and the movable diaphragm for dividing the chamber into first and second compartments. The cassette also includes input lines into the first and second compartments and output lines from the first and second compartments. The cassette further includes valves in the two input lines and valves in the two output lines, the valves being paired to provide for a flow of fluid into one of the compartments and out of the other compartment at first times and the flow of fluid into the other compartment and out of the first compartment at other times. The operation of such valves is coordinated with the movement of the diaphragm so that the flow of fluid into one of the compartments and out of the other compartment, and the direction of movement of the diaphragm in the chamber, is reversed every time that the diaphragm moves to a particular position in one of the compartments.

Figure 1:
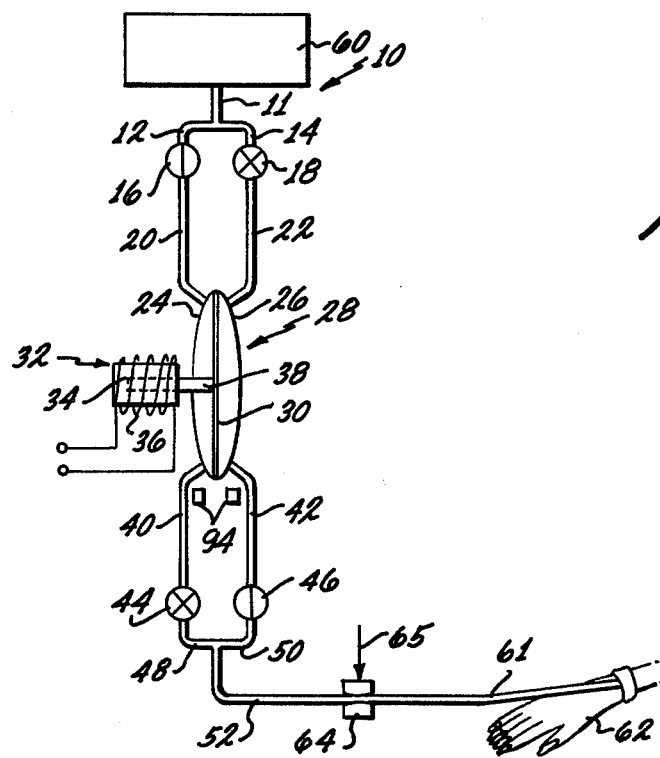
FIG. 1 is a schematic view of certain hydraulic features of a controller constituting this invention when the controller is used to introduce fluid to a patient.

A cassette generally indicated at 10 is shown on a schematic basis in FIG. 1. The cassette may be made from a rigid material such as a rigid plastic material. The cassette includes an input line 11 and a pair of conduits 12 and 14 branching from the input line. Valves 16 and 18 are respectively disposed in the lines 12 and 14 and each valve is operative in open and closed states. Branch lines 20 and 22 respectively extend from the valves 16 and 18 to first and second compartments 24 and 26 in a chamber generally indicated at 28. The compartments 24 and 26 are defined by a separating member 30 extending across the chamber. The separating member is attached at its periphery to the walls of the chamber and is movable between the end walls respectively defining the boundaries of the compartments 24 and 26. The separating means 30 may be made from a thin sheet of a resilient material such as rubber so as to constitute a diaphragm.

A transducer generally indicated at 32 is associated with the diaphragm 30 to indicate the position of the diaphragm at each instant. The transducer 32 may include a hollow enlargement or bulb 34 which extends from one of the walls of the chamber 28 such as the wall defining the boundary of the compartment 24. The enlargement or bulb 34 is disposed in hermetically sealed relationship to the wall of the compartment 24. The bulb 34 and the wall 24 may be open to each other at their common boundary.

A transducer member such as a coil 36 is wound on the bulb 34. A second transducer member such as a ferrous rod 38 extends from the diaphragm 30 into the hollow confines of the bulb 34 and is movable with the diaphragm. In this way, the inductance of the coil 36 can be varied in accordance with displacements of the diaphragm 30 toward the boundary wall of the compartment 26 or toward the boundary wall of the compartment 24.

Branch lines 40 and 42 respectively extend from the compartments 24 and 26. Valves 44 and 46 are respectively disposed at the ends of the branch lines 40 and 42. Each of the valves 44 and 46 is operative in open and closed states. Branch lines 48 and 50 respectively extend from the valves 44 and 46 to an output line 52.

As will be seen in FIG. 1, the input line 11 is connected to a source 60 of fluid. Similarly, as will be seen in FIG. 1, the output line 52 is connected to an external line 61, which extends to a patient 62 when the cassette is in use. Only the hand and arm of the patient are shown in FIG. 1. A pinch clamp or valve 64 may be coupled to the line 61 to control the rate at which fluid passes to the patient. The pinch clamp 64 is adjustable to control the opening in the line 61. This adjustability is indicated by an arrow 65 in FIG. 1.

In the operation of the cassette, the valves 18 and 44 are paired and the valves 16 and 46 are paired. At any one time, one pair of valves may be open and the other pair of valves may be closed. For example, when the valves 16 and 46 are open, the valves 18 and 44 are closed. At such a time, fluid flows downwardly from the source 60 through the line 11, the valve 16 and the line 20 into the compartment 24. At the same time, fluid flows outwardly from the compartment 26 through the line 42, the valve 46, the line 50 and the lines 52 and 61 to the patient 62. The rate of such flow is controlled by the setting of the pinch clamp 64. Since fluid flows into the compartment 26 and out of the compartment 24, the diaphragm 30 is flexed to the right in FIG. 5. This causes the rod 38 to move outwardly from the coil 36 so that the inductance of the coil decreases.

Similarly, when the valves 16 and 46 are closed, the valves 18 and 44 are open. At such a time, fluid flows downwardly from the source 60 through the line 11, the line 14, the valve 18 and the line 22 into the compartment 26. At the same time, fluid flows outwardly from the compartment 24 to the patient 62 through the line 40, the valve 44, the line 48 and the lines 52 and 61. The rate of such flow is also controlled by the setting of the pinch clamp 64. Since fluid flows into the compartment 26 and out of the compartment 24, the diaphragm 30 is flexed to the left in FIG. 1 so that the rod 38 moves into the coil 36. This causes the inductance of the coil 36 to increase.

Figure 2:
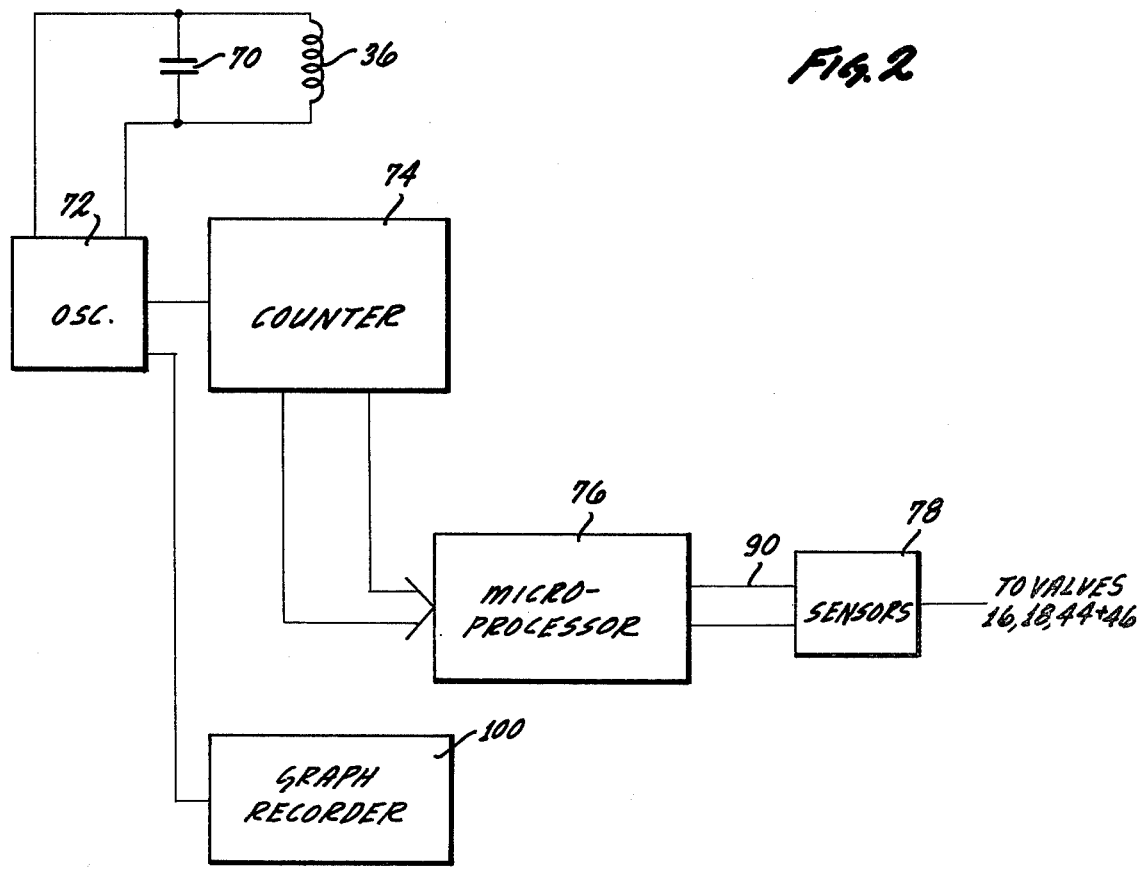
FIG. 2 is a circuit diagram, primarily in block form, of certain electronic features in the controller shown in FIG. 1.
Figure 3:
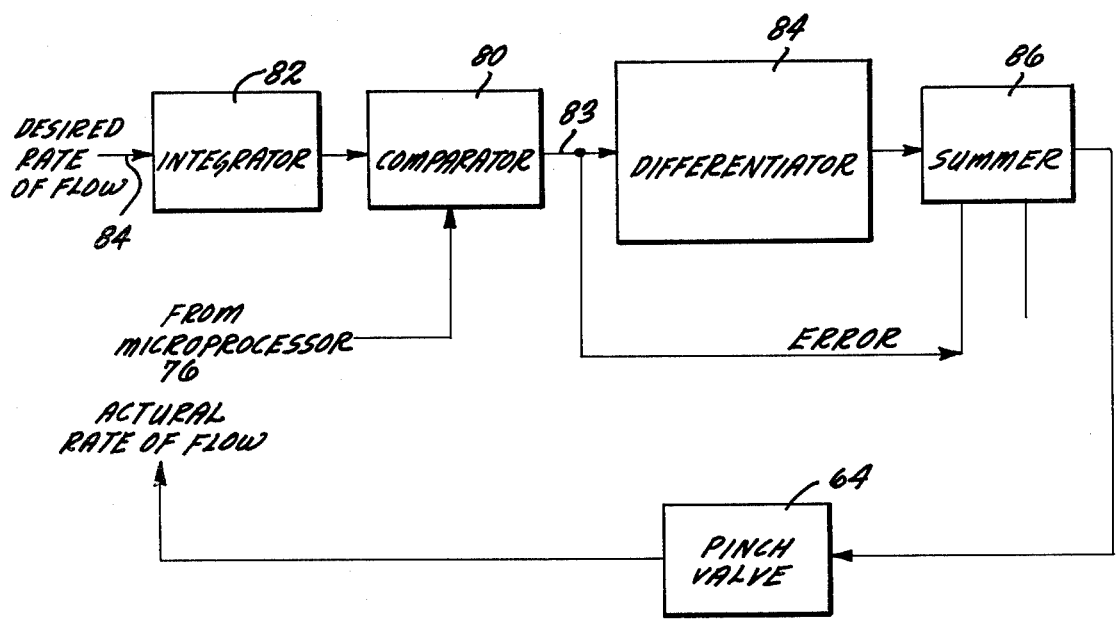
FIG. 3 is a circuit diagram, partly in block form, of other features, including other electronic features, in the system shown in FIGS. 1 and 2.

The cassette is included in a system shown in block form in FIGS. 2 and 3. The system shown in FIGS. 2 and 3 includes the coil 36, which is connected in a parallel resonant circuit with a capacitance 70. This parallel resonant circuit is included in an oscillator 72 although it is shown in FIG. 2 as being separate from the oscillator. Since the resonant frequency of the parallel resonant circuit varies in accordance with the inductance of the coil 36, the frequency of the signals from the oscillator varies in accordance with the movements of the diaphragm 30. As a result, the frequency of the signals from the oscillator 72 provides an indication of the positioning of the diaphragm 30 in the chamber 28 at each instant. Furthermore, the signals from the oscillator 72 are introduced to a counter 74 which counts the signals from the oscillator and introduces the signals to a microprocessor 76. The microprocessor 76 processes the signals from the counter 74 to provide an indication at each instant of the volume of fluid flowing through the line 52. Furthermore, the microprocessor 76 may introduce signals on a line 90 to the valves 16, 18, 44 and 46 to operate the valves from one state to the other every time that a particular increment of fluid is introduced to the patient. Alternatively, the valves 16, 18, 44 and 46 may be operated from one state to the other when sensors sense the movement of the diaphragm 30 to a particular position in the compartments 24 and 26. Such sensors are indicated at 94 in FIG. 1.

The signals produced by the microprocessor 76 to represent the actual volume of fluid flow are also introduced to a comparator 80 (FIG. 3) which also received signals from an integrator 82. The integrator 82 receives the signals produced on a line 84 to represent the desired rate of fluid flow. By integrating the signals on the line 84 as a derivative of time, the integrator 82 provides an indication of the desired volume of fluid flow at any instant of time. As will be appreciated, the signals on the line 84 can be varied to represent any desired value of the rate of fluid flow.

The comparator 80 compares the signals representing actual volume of fluid flow at each instant with the desired volume of fluid flow at that instant and produces at each instant an error signal on a line 83. This signal represents the error in the actual volume of fluid flow at each instant relative to the desired volume of fluid flow at that instant. The signal on the line 82 is differentiated by a stage 84 to represent the rate at which the error is being generated.

The signals representing the error in the volume of fluid flow at each instant and the error in the rate of the fluid flow at each instant are added in a summer 86. As will be appreciated, the summer 86 may be included in the microprocessor 76. Such summing may occur on a sophisticated (or weighted) basis in the microprocessor in view of the capabilities available in microprocessors. The resultant signals from the summer 86 are introduced to the pinch valve 64 to adjust the pinch valve in a direction for minimizing the error signals.

As previously described, the microprocessor 76 provides an indication of the cumulative volume of fluid flow at each instant. These signals are processed in the microprocessor 76 so that the microprocessor produces a signal on a line 90 every time that the cumulative value of the fluid flow reaches a value which is an integral multiple of a particular base value. This particular base value represents the total amount of fluid which it is desired to introduce to the patient from each compartment in each movement of the diaphragm 30 in a particular direction. Every time that a signal is produced on the line 90, the direction of movement of the diaphragm 30 is reversed so that fluid flows into the particular compartment and flows out of the other compartment. Thus, in alternate cycles, fluid flows into the first compartment and out of the second compartment in a particular volume and, in the other cycles, fluid flows into the second compartment and out of the first compartment in the particular volume. Thus, although the pinch clamp 64 controls the rate of fluid flow at each instant, the volumetric accuracy of the flow of fluid results primarily from the flow of particular amounts of fluid through the compartments 24 and 26 in each cycle of operation.

The flow of a particular amount of fluid to the patient in each directional movement of the diaphragm 30 is accomplished by operating the valves 16, 18, 44 and 46 in accordance with the successive signals on the line 90 so that, in alternate cycles, the valves 16 and 46 are opened and the valves 18 and 44 are closed and, in the other cycles, the valves 16 and 46 are closed and the valves 18 and 44 are opened. Actually, after each operation of the valves in one cycle of fluid flow, all of the valves 16, 18, 44 and 46 are preferably closed for a brief instant to stabilize the operation of the system before the next cycle of operation is initiated by opening one of the pairs of valves 16 and 46 or 18 and 44. As will be appreciated, the operation of the other pair of valves is not affected since such pair of valves is maintained closed. The closing of all of the valves before the selective opening of one pair is within the capabilities of the microprocessor. As will be appreciated, this closing of all of the valves can be accomplished mechanically under the control of the microprocessor such as by cams.

The reciprocal movement of the diaphragm 30 in the chamber 28 does not occur at a high rate. For example, the maximum rate of the reciprocal excursions of the diaphragm 30 may be in the order of five hundred (500) or more per hour. The minimum rate of such reciprocal excursions may be in the order of one (1) per hour. With the diaphragm 30 in a neutral position, the cumulative volume of each of the compartments 24 and 26 may be in the order of one half ($\frac{1}{2}$) of a cubic centimeter or more. This causes the volume of the chamber 28 to be in the order of two (2) cubic centimeters or more. As a result, the volume of fluid introduced to the patient may be varied from a rate slightly less than one (1) cubic centimeter per hour to a rate in the order of three hundred (300) to five hundred (500) cubic centimeters per hour.

Figure 4:
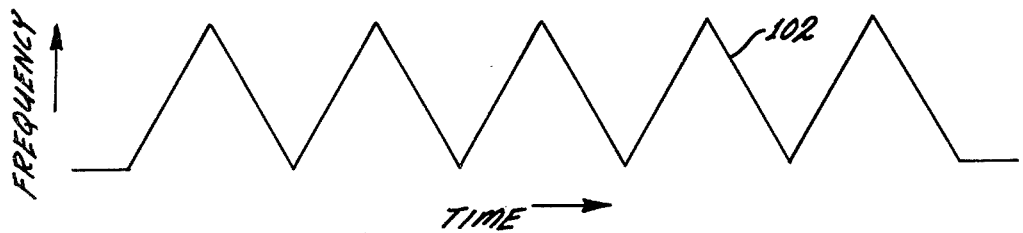
FIG. 4 is a graph illustrating the operation of the system shown in FIGS. 1, 2 and 3 at progressive instants of time in producing variations in a particular parameter such as the frequency of the signals from such system.

FIG. 4 is a graph indicating the volume of fluid flow at each instant as represented by the frequency of the signals from the oscillator 72. In FIG. 4, a graph 102 has an abscissa representing time and an ordinate representing the frequency of the signals in the oscillator 72. As will be seen from FIG. 4, the frequency of the signals in the oscillator 72 varies on a linear basis with time between maximum and minimum values. This corresponds to the movement of the diaphragm 30 on a reciprocal basis to produce a displacement of the rod 38 into the coil 36 and then out of the coil. As will be seen from FIG. 4, the graph 102 is saw-toothed in shape, thereby indicating that the flow of fluid to the patient occurs at a constant rate.

The controller described above has certain important advantages. It provides for a flow of fluid such as intravenous fluid on a gravitational basis to a patient at a precise and predetermined rate. Flow of fluid on a gravitational basis to a patient is advantageous because fluid flows only when the system is operative since fluid is not being forced into the patient such as sometimes occurs when pumps are used. Furthermore, contrary to the controllers of the prior art, rates of fluid flow are obtained by the controller of this invention with an accuracy significantly greater than corresponding controllers of the prior art.

The controller described above also has other advantages of some importance. It includes a cassette which is easy to operate and which is easily replaceable in the system. In this way, the unit of the cassette previously used in the controller can be replaced by a previously sterilized and fully hygienic unit every time that the system is to be used to introduce fluid to a new patient. The controller and the cassette are particularly advantageous because only the cassette receives the flow of fluid from the source and passes the fluid to the patient. Since the controller does not receive any of the fluid flow, it can be placed into use with each new patient without any need to sterilize the controller and with only the requirement that the new unit of the cassette be inserted into the controller.

The replaceable cassette is shown primarily in FIG. 1. Such a cassette is fully disclosed and is claimed in application Ser. No. 913,282 filed concurrently with this application by Raymond Cannon and assigned of record to the assignee of record of this application.

Although this application has been disclosed and illustrated with reference to particular applications, the principles involved are susceptible of numerous other applications which will be apparent to persons skilled in the art. The invention is, therefore, to be limited only as indicated by the scope of the appended claims.

I claim:

1. In combination in a system for providing a controlled introduction of fluid from a source to a patient,
    first means for storing the fluid, the first means including first and second compartments and a diaphragm separating the compartments and movable in the first means to vary the volumes of the first and second compartments,
    second means operatively coupled to the first and second compartments for providing a first times for the introduction of fluid from the source to the first compartment and the passage of fluid from the second compartment to the patient and at other times for the introduction of fluid from the source to the second compartment and the passage of fluid from the first compartment to the patient, and
    third means responsive to the movement of the diaphragm to a particular position in the second compartment for operating on the second means to obtaining the introduction of fluid from the source to the first compartment and the passage of fluid from the second compartment to the patient and responsive to the movement of the diaphragm to a particular position in the first compartment for operating on the second means to obtain the introduction of fluid from the source to the second compartment and the passage of fluid from the first compartment to the patient.

2. The combination set forth in claim 1, including, a conduit extending from the second means to the patient, adjustable means operatively coupled to the second means for controlling the flow of fluid through the conduit, means for providing a desired rate of flow of the fluid to the patient, means responsive to the movements of the diaphragm for providing an indication of the actual rate of flow to the patient, and means responsive to the desired and actual rates of flow of the fluid to the patient for adjusting the adjustable means to control the actual rate of flow to the patient in accordance with any differences between the actual and desired rates.

3. The combination set forth in claim 2, including, transducer means responsive to the movement of the diaphragm for producing a variable impedance in accordance with such movement, means responsive to the variable impedance provided by the transducer means for producing signals having a variable frequency in accordance with such impedance variations, and means responsive to the variable frequency of the signals for indicating the position of the diaphragm at each instant and the rate of flow of the fluid to the patient.

4. In combination in a system for providing a controlled introduction of fluid from a source to a patient, first and second storage means, first means operatively coupled to the first and second storage means and having first and second states of operation and operative in the first state for providing for a flow of fluid from the source to the first storage means and a simultaneous flow of fluid from the second storage means to the patient and operative in the second state for providing for a flow of fluid from the source to the second storage means and a simultaneous flow of fluid from the first storage means to the patient, and second means operatively coupled to the first means and responsive to cumulative flows of fluid from each of the first and second storage means for alternately producing an operation of the first means in the first and second states.

5. The combination set forth in claim 4 wherein the second means is responsive, in the first state of operation of the first means, to the flow of a particular amount of fluid to the first storage means and from the second storage means to produce an operation of the first means in the second state and is responsive, in the second state of operation of the first means, to the flow of a particular amount of fluid to the second storage means and from the first storage means to produce an operation of the first means in the first state.

6. The combination set forth in claim 5, including, the first and second storage means being defined by a chamber and a diaphragm movable in the chamber to increase the volume of one of the storage means and correspondingly decrease the volume of the other storage means, and the second means being responsive to each movement of the diaphragm to a particular position in the first compartment to initiate an operation of the first means in the second state and being responsive to each movement of the diaphragm to a particular position in the second compartment to initiate an operation of the first means in the first state.

7. The combination set forth in claim 5, including, control means adjustable to control the rate at which fluid passes from the first means to the patient, and third means responsive to the rate of flow of fluid to the patient for adjusting the control means to maintain the flow of the fluid to the patient at a particular rate.

8. The combination set forth in claim 7, including, the first means including an output line extending to the patient and the control means including an adjustable clamp for pinching the line to control the rate at which fluid flows through the output line to the patient, and the third means including means adjustable to provide a desired rate at which fluid flows to the patient, means responsive to the flow of fluid to the patient for indicating the rate of such flow, means responsive to the indications of the desired and actual rates of fluid flow for comparing such indications to produce an error signal in accordance with any differences in such indications, and means reponsive to the error signal for adjusting the clamping action of the clamp on the output line to minimize the error signal.

9. In combination in a system for providing a controlled introduction of fluid from a source to a patient, first means for storing the fluid, the storing means including a movable diaphragm for dividing the storing means into first and second compartments, second means for providing for an introduction of fluid from the source to one of the compartments and for providing for the passage of fluid from the other compartment to the patient, first adjustable means for controlling the rate at which fluid passes from the second means to the patient, second adjustable means for providing a desired rate at which fluid is to pass to the patient, third means operatively coupled to the second means for indicating the rate at which fluid is actually flowing to the patient, fourth means operatively coupled to the second adjustable means and to the third means and responsive to the indications of the desired and actual rates of fluid flow for producing an error signal in accordance with any differences in such signals, fifth means reponsive to the error signals for producing adjustments in the first adjustable means to minimize such error signals, and sixth means operatively coupled to the second means and responsive to the flow of fluid to the patient for providing at first times for the introduction of fluid into the first compartment and the passage of fluid from the second compartment and, at second times alternating with the first times, for the introduction of fluid into the second compartment and the passage of fluid from the first compartment.

10. The combination set forth in claim 9, includng, the first means including an output line to the patient, the first adjustable means including a clamp adjustable on the output line to control the rate at which fluid flows through the output line, and the fifth means including means for controlling the clamping of the first adjustable means on the output line.

11. The combination set forth in claim 9, including, the first means constituting a replaceable cassette and the storage means constituting a chamber in the cassette and the movable diaphragm extending across the chamber to divide the chamber into first and second compartments and the diaphragm being resilient for movement across the chamber to increase the volume of one of the compartments and correspondingly decrease the volume of the other compartment.

12. The combination set forth in claim 11, including, the sixth means including valve means disposed in the cassette and operative in first and second relationships and operative in the first relationship to provide for the introduction of fluid into the first compartment and the passage of fluid from the second compartment and operative in the second relationship to provide for the introduction of fluid into the second compartment and the passage of fluid from the first compartment.

13. The combination set forth in claim 12, including, the sixth means including a first pair of valves each having first and second operative relationships, a first one of the valves in the first pair providing in the first operative relationship for the introduction of fluid into the first compartment from the source and preventing in the second operative relationship the introduction of fluid into the first compartment from the source, the other valve in the first pair providing in the first operative relationship for the passage of fluid from the second compartment to the patient and preventing in the second operative relationship the passage of fluid from the second compartment to the source, the sixth means including a second pair of valves each having first and second operative relationships, a first one of the valves in the second pair providing in the first operative relationship for the introduction of fluid into the second compartment from the source and preventing in the second operative relationship the introduction of fluid into the second compartment from the source, the other valve in the second pair providing in the first operative relationship for the passage of fluid from the first compartment to the patient and preventing in the second operative relationship the passage of fluid from the first compartment to the source, and the sixth means being responsive to the movement of the diaphragm to a particular position in a direction to reduce the size of the first compartment for producing an operation of the valves in the first pair in the first relationship and an operation of the valves in the second pair in the second relationship and being responsive to the movement of the diaphragm to a position in a direction to reduce the size of the second compartment for producing an operation of the valves in the second pair in the first relationship and an operation of the valves in the first pair in the second relationship.

14. In combination in a system for providing a controlled introduction of fluid from a source to a patient, storage means constructed to provide a flow into the storage means from first and second operative directions and to provide a flow from the storage means from first and second opposite directions, first means for providing for an introduction of fluid from the source into the storage means in the first and second opposite directions, second means for providing for a passage of fluid from the storage means to the patient in the first and second opposite directions, valve means operatively coupled to the storage means and having first and second operative relationships and operative in the first relationship to provide for a flow of fluid into the storage means only in the first direction and a passage of fluid from the storage means only in the second direction and operative in the second relationship to provide for a flow of fluid into the storage means only in the second direction and a passage of fluid from the storage means only in the first direction, and means responsive to the flows of particular amounts of the fluid into and out of the storage means in one of the first and second operative relationships for reversing the operation of the valve means to the other one of the first and second operative relationships.

15. The combination set forth in claim 14, including, the storage means being constructed to define first and second compartments and the flow in the first and second directions into the storage means respectively being into the first and second compartments and the flow in the second and second directions from the storage means being respectively from the first and second compartments.

16. The combination set forth in claim 15, including, the valve means being operative in the first relationship to provide for the flow of fluid into the first compartment and out of the second compartment and being operative in the second relationship to provide for the flow into the second compartment and out of the first compartment.

17. The combination set forth in claim 16, including, the reversing means being operatively associated with the storage means for providing for a flow at each instant of the same amount of fluid into one of the first and second compartments and from the other one of the first and second compartments.

18. The combination set forth in claim 17, including, the reversing means also being operative to reverse the operative of the valve means from one of the first and second relationships to the other one of the first and second relationships upon each flow of a particular amount of fluid into one of the compartments and out of the other one of the compartments.

19. The combination set forth in claim 18, including, the first providing means including an input line and a first pair of branch lines respectively extending from the input line to the first and second compartments, the second providing means including a second pair of branch lines respectively extending from the first and second compartments and an output line communicating with the second pair of branch lines.

20. The combination set forth in claim 19, including, the valve means including a plurality of valves each disposed in an individual one of the branch lines in the first and second pairs and operative to control the flow of fluid through the associated one of the branch lines in accordance with the operation of the valve means in the first and second relationships.

21. In combination in a system for providing a controlled introduction of fluid from a source to a patient, means for providing an indication of a desired rate for introducing fluid into a patient, means responsive to the flow of fluid for providing an indication of the rate at which fluid is flowing into the patient, means responsive to the indications of the desired and actual rates of flow for producing an error signal having characteristics representing any differences in such indications, means including a replaceable cassette for providing a reservoir for the controlled storage of fluid flowing from the source and for the controlled flow of the stored fluid to the patient, an output line extending from the replaceable cassette for introducing fluid from the reservoir to the patient, an input line extending to the replaceable cassette for introducing fluid to the reservoir from the source, and means associated with the output line and responsive to the error signal for adjustably controlling the rate at which fluid flows from the reservoir through the output line to the patient in accordance with the characteristics of the error signal.

22. The combination set forth in claim 21 wherein the reservoir has first and second ends and the means including the cassette includes means for providing for the introduction of fluid to the reservoir at a particular one of the first and second ends and for providing for the passage of fluid from the reservoir at the other one of the first and second ends and for obtaining a reversal of the particular one of the first and second ends for providing for the introduction of fluid into the reservoir and a reversal of the other one of the first and second ends for the passage of fluid from the reservoir to the patient.

23. The combination set forth in claim 22 wherein the means including the cassette includes valve means having first and second operative relationships and operative in the first relationship to provide for an introduction of fluid to the first end of the reservoir and a passage of fluid from the second end of the reservoir and operative in the second relationship to provide for an introduction of fluid to the second end of the reservoir and a passage of fluid from the first end of the reservoir.

24. The combination set forth in claim 23, including, the means including the cassette including means for providing for a reversal of the valve means between the first and second operative relationships every time that a particular amount of fluid flows from the reservoir to the patient.

25. In combination in a systen for providing a controlled introduction of fluid from a source to a patient, means for providing an indication of a desired rate for introducing fluid to a patient, means responsive to the flow of fluid for providing an indication of the rate at which fluid is flowing to the patient, means responsive to the indications of the desired and actual rate of flow for producing an error signal having characteristics representing any differences in such indications, means for providing a reservoir for the storage of fluid and for the controlled flow of fluid from the source and for the controlled flow of fluid to the patient and for the flow of fluid to the reservoir at the same rate as the flow of fluid from the reservoir, an input line for introducing fluid from the source to the reservoir, an output line for introducing fluid from the reservoir to the patient, and means associated with the output line and responsive to the error signal for adjustably controlling the rate at which fluid flows from the reservoir through the output line to the patient.

26. The combination set forth in claim 25, including, resilient means being disposed in the reservoir for dividing the reservoir into first and second compartments, means operatively associated with the reservoir for providing for the introduction of fluid into one of the compartments and the simultaneous flow of fluid from the other compartment, and means operatively associated with the last mentioned means and responsive to particular cumulative increases in the volume of fluid flowing to a patient to reverse the particular one of the compartments receiving the flow of fluid from the source and the other one of the compartments providing for the flow of fluid to the patient.

27. The combination set forth in claim 26, including, each of the first and second compartments having an individual conduit extending from the input line and having an individual conduit extending to the output line and the reversing means including a plurality of valves each disposed in an individual one of the lines and having first and second states of operation and operative in the first state to provide for a flow of flow through the associated conduit and operative in the second state to prevent the flow of fluid through the associated conduit.

28. The combination set forth in claim 27, including, the valves being paired to provide for an operation at each instant of the valves in one pair in the first state and the operation of the valves in the other pair in the second state and one of the valves in each pair being associated with an individual one of the conduits extending from the input line and the other valve in each pair being associated with an individual one of the conduits extending to the output line.

29. In combination in a system for providing a controlled introduction of fluid from a source to a patient, means for providing an indication of a desired rate for introducing fluid to a patient, means responsive to the flow of fluid for providing an indication of the rate at which fluid is flowing to the patient, means responsive to the indications of the desired and actual rates of flow for producing an error signal having characteristics representing any differences in such indications, means for providing a reservoir for the fluid, means for providing for a flow of fluid from the reservoir to the patient, means operatively coupled to the last-mentioned means and responsive to the error signal for adjusting the rate of the flow of fluid from the reservoir to the patient in accordance with the characteristics of such error signal, and means for providing for the introduction of fluid from the source to the reservoir to replenish the fluid flowing from the reservoir to the patient.

30. The combination set forth in claim 29 wherein the means for providing for the flow of fluid to the patient includes an output line having an orifice for the flow of fluid and the means for adjusting the rate of such fluid flow includes an adjustable clamp for controlling the size of the orifice in the output line.

31. In combination in a system for providing a controlled introduction of fluid from a source to a patient, means for providing a first signal representing at each instant a desired flow of the fluid from the source to the patient, means responsive to the first signal for integrating the signal to provide an indication of the cumulative amount of fluid flow desired at each instant, conduit means for providing for a controlled flow of fluid from the source to the patient, means for providing a second signal representing at each instant the actual flow of fluid from the source to the patient at that instant, means responsive to the second signal for integrating the second signal to provide an indication of the cumulative amount of fluid actually flowing to the patient, means responsive to the indications representing the cumulative values of the actual and desired flows of fluid to the patient for producing an error signal representative of such differences, and means responsive to the error signal for adjusting the conduit means in a direction for varying the fluid flow through the conduit means to minimize the error signal.

32. The combination set forth in claim 31, including, means responsive to the error signal for differentiating the error signal to indicate rate of change in the error signal, and means for summing the error signal and the differentiated error signal to produce a composite signal, the adjusting means for the conduit means being responsive to the composite signal to adjust the flow of fluid through the conduit means in a direction to minimize the composite signal.

33. The combination set forth in claim 31 wherein the conduit means constitutes a plastic tube and wherein the adjustable means pinches the tube in accordance with the characteristics of the error signal.

34. The combination set forth in claim 32 wherein the conduit means constitutes a plastic tube and wherein the adjustable means pinches the tube in accordance with the characteristics of the composite signal and wherein the error signal means constitutes a comparator for comparing the cumulative values of the actual and desired flows of fluid to the patient for producing the composite signal.

35. In combination in a system for providing a controlled introduction of fluid from a source to a patient, means for providing a first signal representing at each instant a desired flow of the fluid from the source to the patient, conduit means for providing for a flow of fluid from the source to the patient, means operatively coupled to the conduit means for adjustably pinching the conduit means to control the rate at which the fluid flows from the source to the patient, means operatively coupled to the conduit means for providing a second signal representing at each instant the actual flow of fluid from the source to the patient, comparator means responsive to the first and second signals for comparing these signals to produce an error signal representing any differences between the first and second signals, and means responsive to the error signal for adjusting the pinching of the conduit means in a direction to minimize the error signal.

36. The combination set forth in claim 35 wherein the conduit means constitutes a plastic tube and the adjusting means pinches the tube to control the orifice in the tube.

* * * * *